United States Patent [19]

Carroll et al.

[11] Patent Number: 4,959,547

[45] Date of Patent: Sep. 25, 1990

[54] APPARATUS AND METHODS FOR DETECTING, LOCALIZING, AND IMAGING OF RADIATION IN BIOLOGICAL SYSTEMS

[75] Inventors: Robert G. Carroll, Largo, Fla.; Robin A. Wise, Jr., Morgan Hill, Calif.

[73] Assignee: Care Wise Medical Products Corporation, Morgan Hill, Calif.

[21] Appl. No.: 363,243

[22] Filed: Jun. 8, 1989

[51] Int. Cl.⁵ .............................................. G01T 1/161
[52] U.S. Cl. .............................. 250/336.1; 250/363.10; 250/505.1
[58] Field of Search .............. 250/336.1, 363.10, 505.1

[56] References Cited

U.S. PATENT DOCUMENTS

| | | | |
|---|---|---|---|
| 3,112,402 | 11/1963 | Okun et al. | 378/147 |
| 3,310,675 | 3/1967 | Prickett et al. | 378/147 |
| 3,609,370 | 9/1971 | Peyser | 378/153 |
| 3,628,021 | 12/1971 | MacDonald | 378/147 |
| 3,863,623 | 2/1975 | Trueblood et al. | 128/654 |
| 3,869,615 | 3/1975 | Hoover et al. | 378/146 |
| 3,919,559 | 11/1975 | Stevens | 378/154 |
| 3,936,646 | 2/1976 | Jonker | 378/148 |
| 4,340,818 | 7/1982 | Barnes | 378/155 |
| 4,419,585 | 12/1983 | Strauss et al. | 250/505.1 |
| 4,489,426 | 12/1984 | Grass et al. | 378/150 |
| 4,502,147 | 2/1985 | Michaels | 378/206 |
| 4,782,840 | 11/1988 | Martin, Jr. et al. | 128/654 |
| 4,801,803 | 1/1989 | Denen et al. | 250/336.1 |

FOREIGN PATENT DOCUMENTS 58-18180  2/1983  Japan ............................... 250/363.10

OTHER PUBLICATIONS

R. A. Bochman, G. R. Fischer and R. R. Hebard, "Variable Aperture Radiation Shield," *IBM Technical Disclosure Bulletin*, vol. 13, No. 1 (Jun. 1970), pp. 166–167.
Abraham E. Cohen, "Gamma-Ray Pinhole Television Camera," *The Review of Scientific Instruments*, vol. 31, No. 1 (Jan. 1960), pp. 29–31.
Merrill A. Bender and Monte Blau, "A Versatile, High-Contrast Photoscanner for the Localization of Human Tumors with Radioisotopes," *International Journal of Applied Radiation and Isotopes*, vol. 4 (1959), pp. 154–161.
Bertram Selverstone, M.D., William H. Sweet, M.D. and Charles V. Robinson, Ph.D., "The Clinical Use of Radioactive Phosphorus in the Surgery of Brain Tumors," *Annals of Surgery*, vol. 130, No. 4 (Oct. 1949), pp. 643–651.

*Primary Examiner*—Constantine Hannaher
*Attorney, Agent, or Firm*—Caesar, Rivise, Bernstein, Cohen & Pokotilow

[57] ABSTRACT

A collimating probe and methods of use for detecting, localizing, and mapping or imaging radiation emanating from a hidden source, such as within the body of a living being. The probe comprises a radiation detector and an adjustment mechanism for adjusting the solid angle through which radiation may pass to the detector. That solid angle is continuously variable. The probe is constructed so that the only radiation reaching the detector is that which is within said solid angle. By adjusting the solid angle from a maximum to a minimum while moving the probe adjacent the source of radiation and sensing the detected radiation, one is able to precisely locate the probe at the source of radiation. The probe can be used for diagnostic or therapeutic purposes. A receptacle is also provided to hold a specimen on the probe to detect the presence of radiation emanating therefrom. A printer and RS 232 data ports are provided. This collimating probe is typically used with the same radiopharmaceuticals used for nuclear medicine imaging.

45 Claims, 8 Drawing Sheets

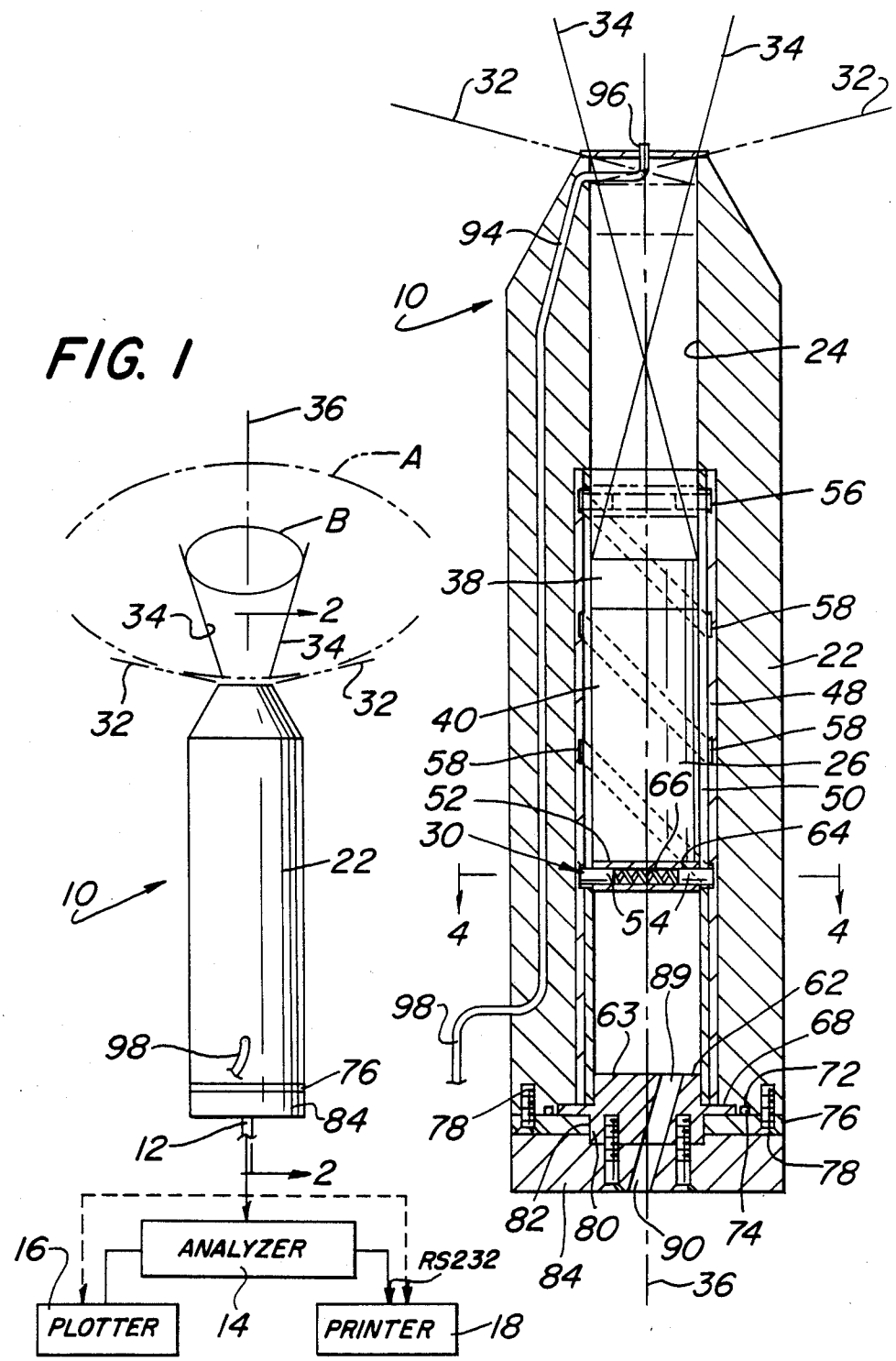

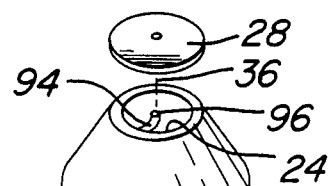
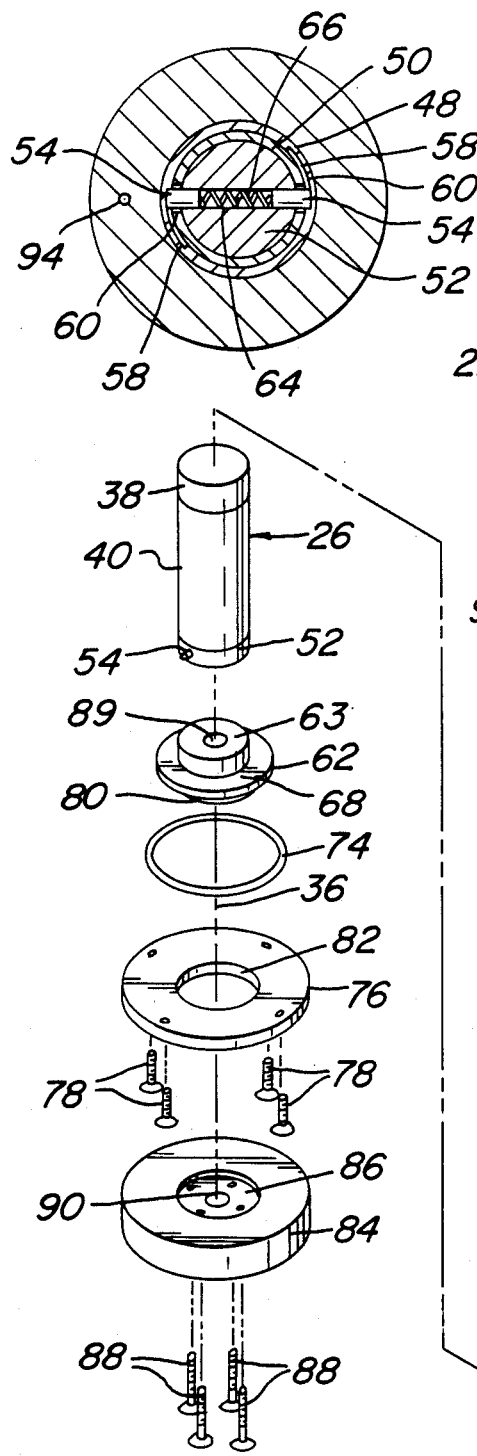
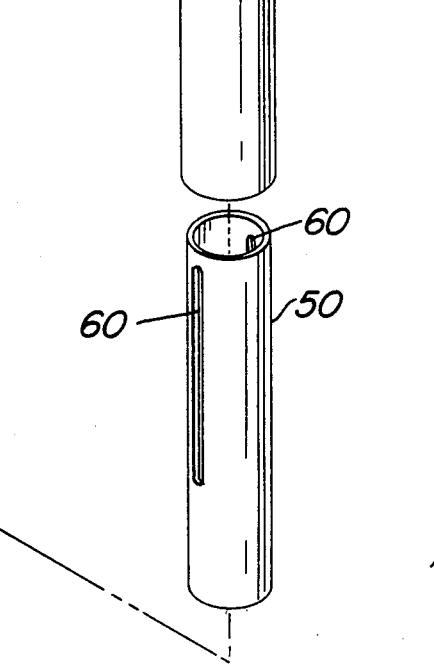

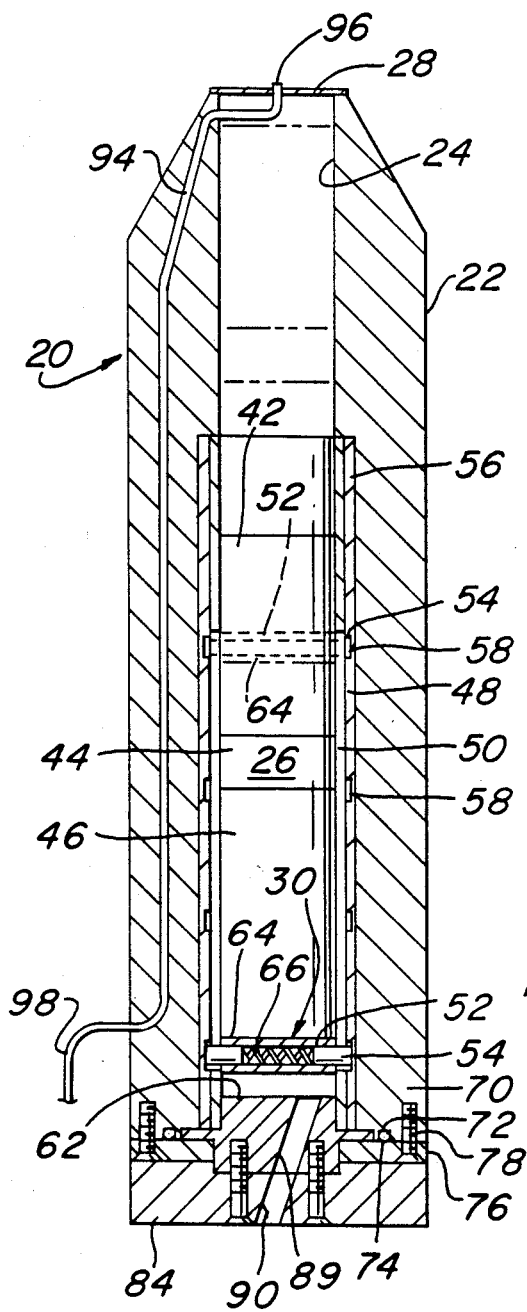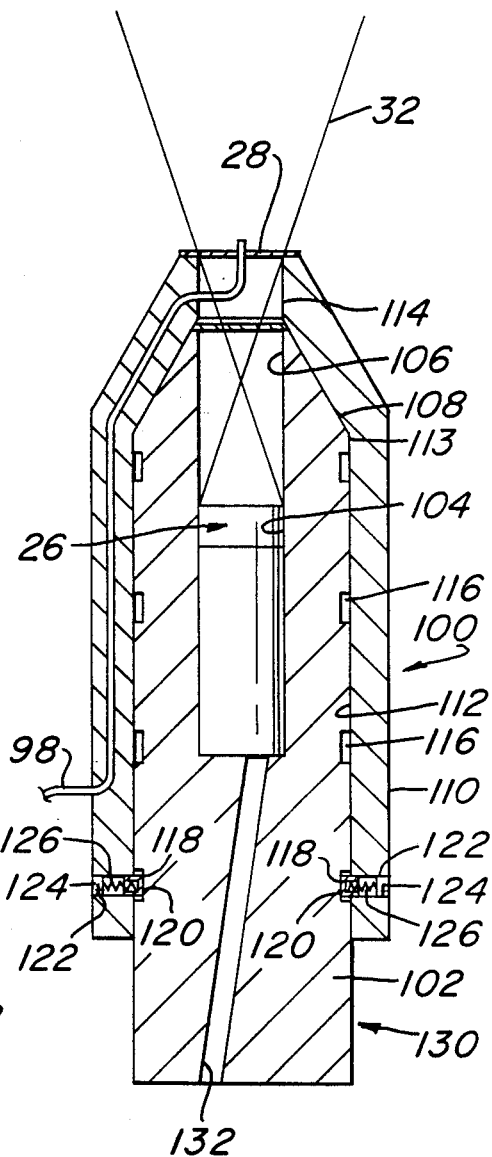

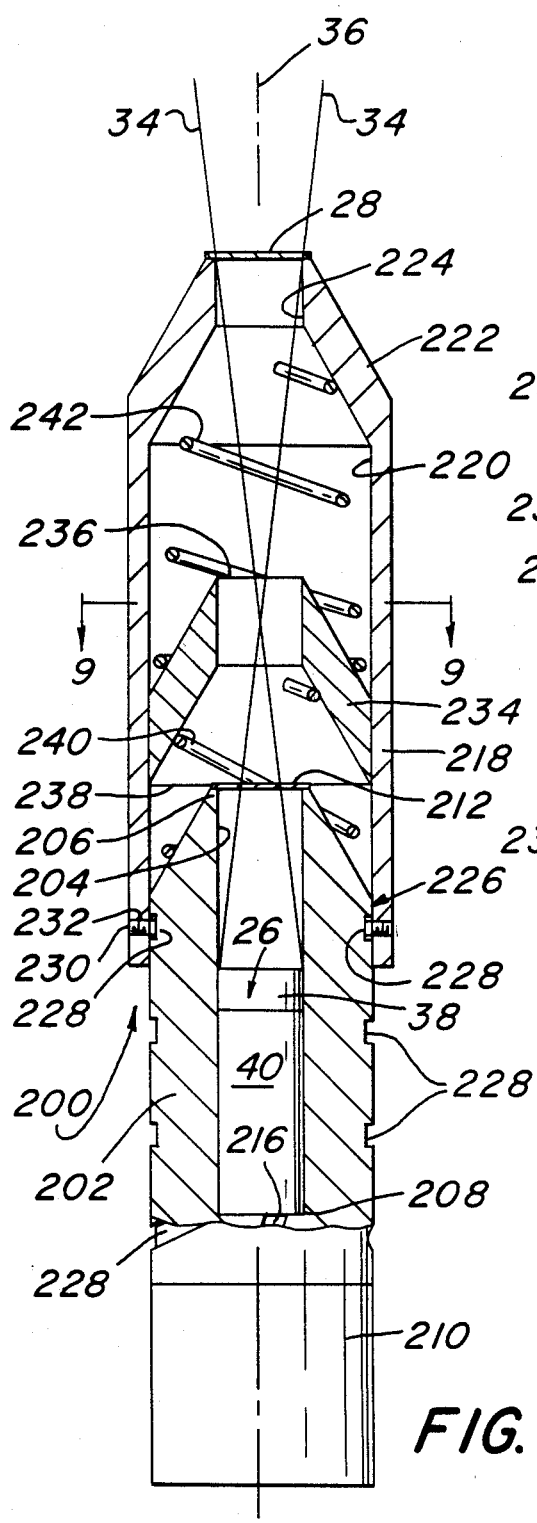
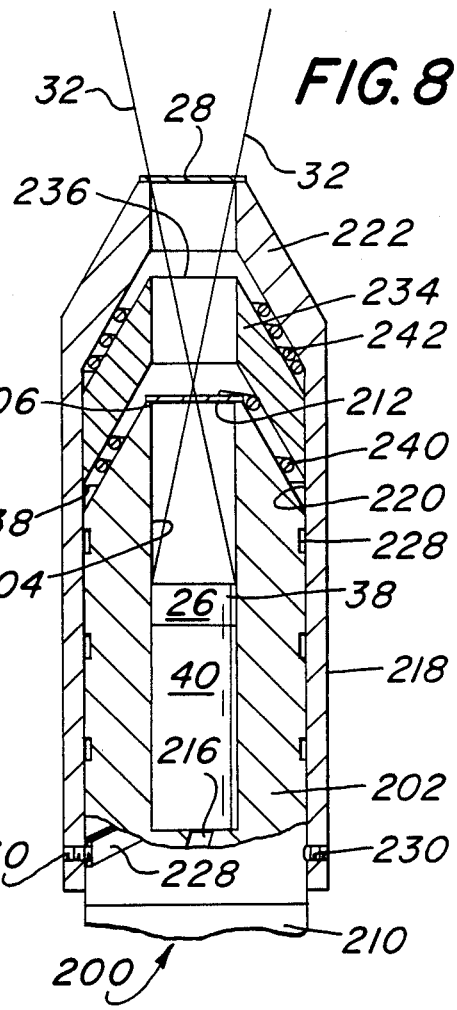
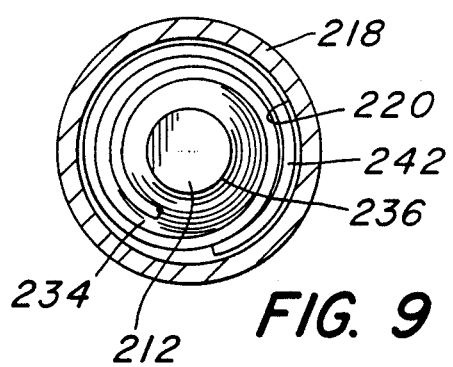

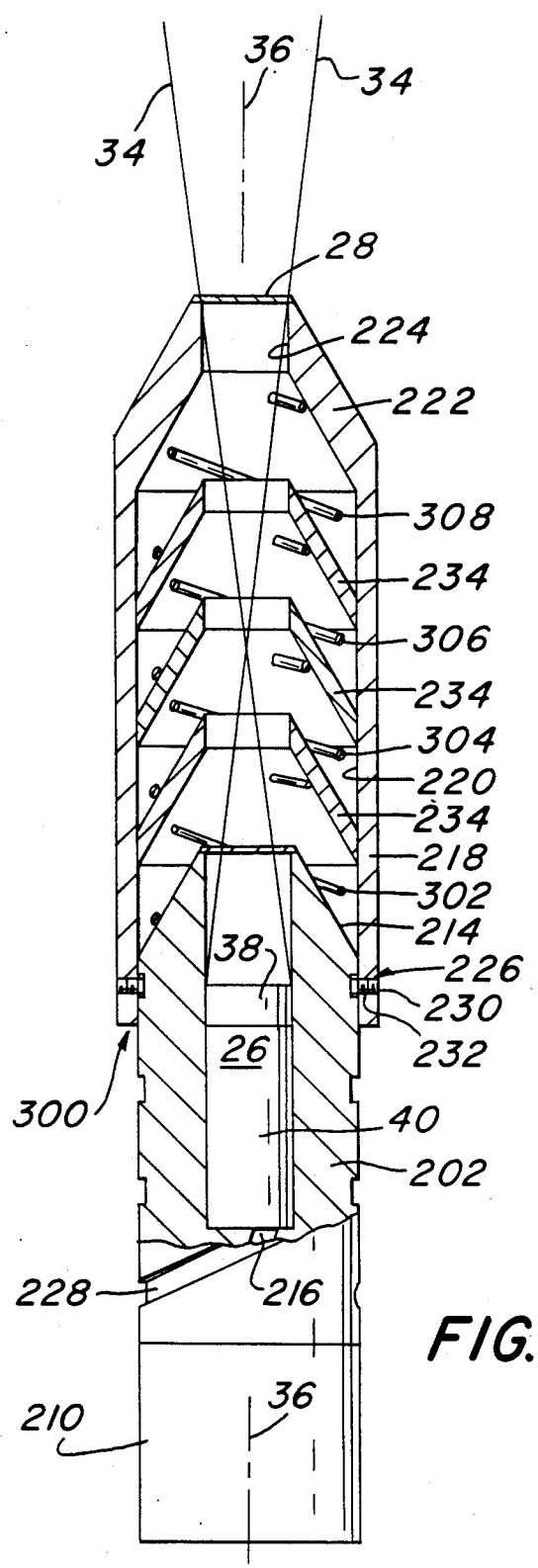
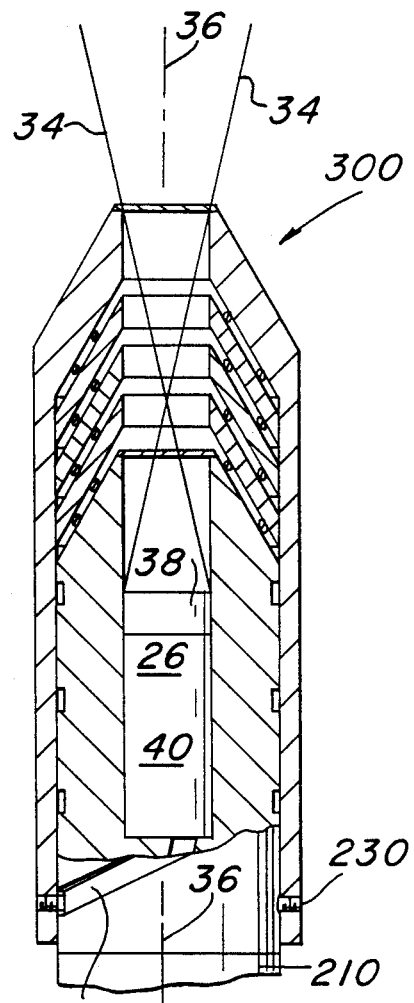
FIG. 10
FIG. 11

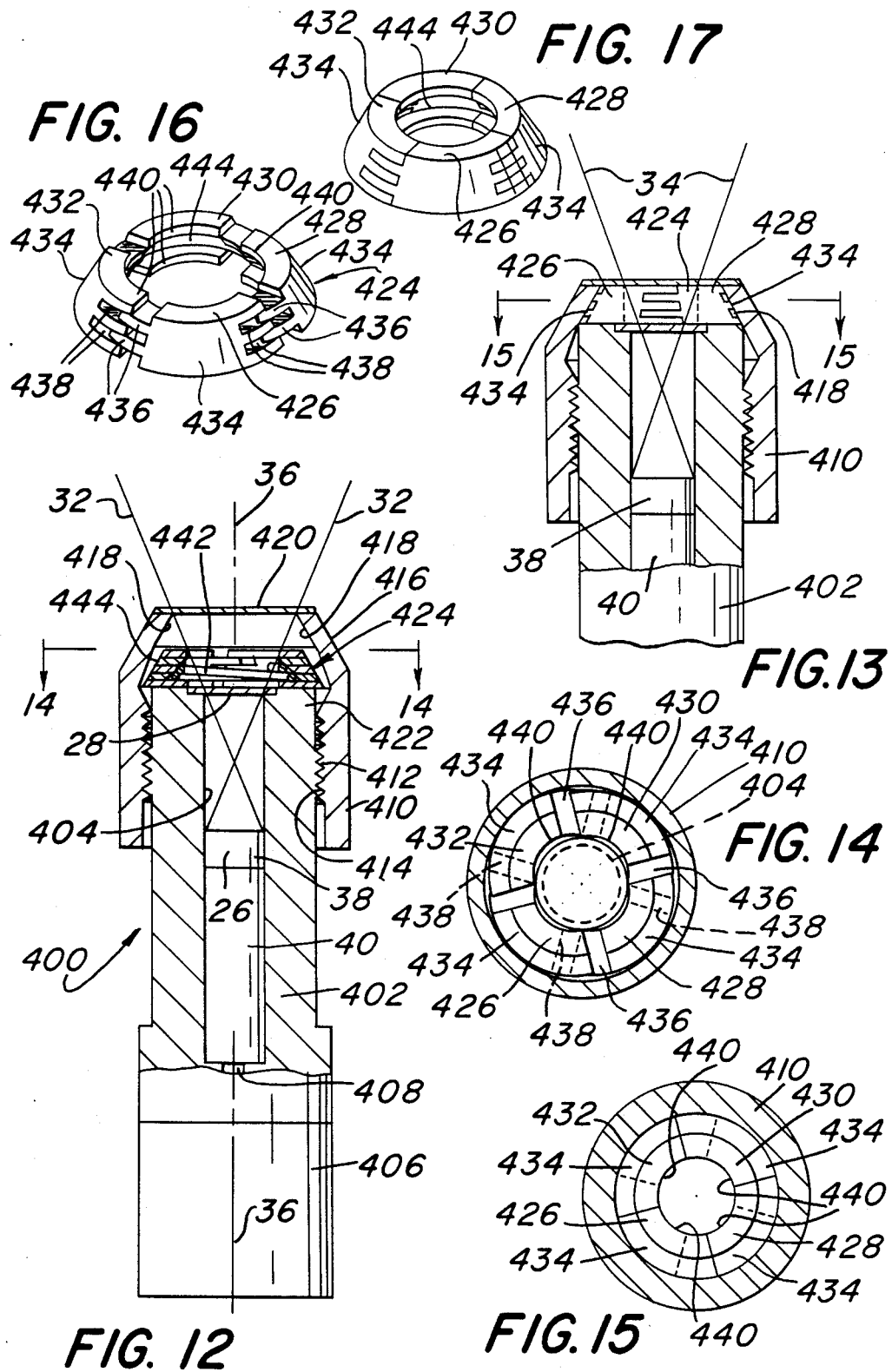

APPARATUS AND METHODS FOR DETECTING, LOCALIZING, AND IMAGING OF RADIATION IN BIOLOGICAL SYSTEMS

BACKGROUND OF THE INVENTION

This invention relates generally to apparatus and methods for detecting radiation, and more particularly to collimating probes and methods of their use for detecting, localizing, and imaging or mapping of radiation in biological systems or other system. Completeness of shielding of the radiation detector from all directions other than through the orifice of the collimator is significant in this invention.

The use of radioactive materials to tag tissue within a patient for effecting its localization and demarcation by radiation detecting devices has been disclosed in the medical literature for at least forty years. For example, in the 1949 Annals of Surgery, there appears an article entitled "The Clinical Use of Radioactive Phosphorous in Surgery and Brain Tumors", by Burtrum Selverstern, William Sweet, and Charles Robinson. That article discloses the use of Geiger Muller counters employed in the localization and demarcation of cerebral tumors.

Significant developments in the localization and demarcation of tissue bearing radioactive isotope tags for diagnostic and/or therapeutic purposes have occurred since that time. Thus, it is now becoming an established modality in the diagnosis and/or treatment of certain diseases, e.g., cancer, to introduce monoclonal antibodies tagged with a radioactive isotope (e.g., Iodine 131, Indium 111, Technetium 99m, etc.) into the body of the patient. Such monoclonal antibodies tend to seek out particular tissue, such as the cancerous tissue, so that the gamma radiation emitted by the isotope can be detected by some apparatus, e.g., Gamma Camera, to provide an image of the radiation emitting tissue.

As is known Gamma Camera imaging apparatus are extremely large, and thus not suitable for use in an operating room. Thus, while the surgeon may be able to utilize some hard copy image or data regarding the location of radioactively tagged tissue provided by Gamma Camera during the surgical procedure the surgeon will, nevertheless, want to manually explore various possible sites that may contain cancerous tissue to ensure that no such tissue has been overlooked or missed. Such action is typically accomplished visually and/or by palpation. Obviously, such inspection procedures are complicated by the limited amount of time available to the surgeon during the surgery, the type of cancer involved, and its possible location(s).

For example, to detect colon cancer the ability to manually pinpoint the location of the cancer is complicated by the fact that the abdominal cavity is bounded on the back by the peritoneum and behind that are the kidneys and the ureters and a significant number of lymph nodes. Surgeons are reluctant to enter the retroperitoneum unless they are reasonably sure that some cancerous tissue is there since entry into the retroperitoneum is fraught with peril of various complications. Nonetheless, there are significant chances that cancer-containing-lymph nodes which aren't big enough to be seen or felt are buried in the retroperitoneal fat. Complicating matters is the fact that the colon is surrounded by fat and the mesentery is surrounded by fat. All of the body structures that might contain tumor-involved-lymph nodes are also likely to contain significant amounts of fat. Therefore finding the tumor-containing lymph nodes among the fat is difficult. The Sigmoid Colon is mobile and can be found from the midline to the left lower abdomen, complicating tumor localization.

One type of apparatus which is small enough to be used in the operating room to assist the surgeon in detecting and localizing the presence of radioactively tagged tissue within the body of the patient makes use of a hand held radiation detecting probe consisting of a detector, shielding, and collimator. Such a probe is disposed or held adjacent to a portion of the patient's body usually exposed during surgical operations where the cancerous tissue is suspected to be in order to detect if any radiation is emanating from that site, thereby indicating that cancerous tissue is likely to be found there. Unfortunately, radiation from the tagged tissue scatters off of the various surrounding body tissue/organs, thereby rendering the localization of the source of the radiation difficult. More importantly, current radiolabelled monoclonal antibodies also localize non-selectively in liver and kidneys, providing intense background activity near tumor sites.

One technique for localizing the radiation source is to look for the highest energy rays emanated by the radioactive isotope. This technique is based on the theory that the lower energy rays received by the probe must have lost energy by scattering, whereas the higher energy rays remaining could not have undergone such scattering and must be coming in a direct line to the detector. While that technique has merit it does not deal with excluding all unscattered rays except those directly in front of the probe orifice.

An additional approach to localize the source of radiation is to utilize some shielding and collimating device with the detector so that the surgeon or operator of the device can adjust the solid angle (cone) in which radiation can be received or accepted by the probe's detector. One such probe and associated device is commercially available from Neoprobe Corporation under the designation Neoprobe 1000. That probe makes use of three collimators, each of which can be attached in either an extended or retracted position on the probe to establish a minimum and maximum solid angle from which radiation can be detected. In particular, each of the Neoprobe 1000's collimators is a device having a different size small diameter opening which is arranged when secured to the probe in the extended position (so that its narrow diameter provides a constrained or narrowed field, i.e., the minimum solid angle of acceptance) to localize the radiation source within a small area. When the collimator is retracted or removed the solid angle of acceptance is maximum, and thus the area from which the radioactivity can be detected is significantly larger. Thus, it is suggested that when using the Neoprobe 1000 that the collimator be removed or retracted for wide angle scanning (e.g., broad survey use), and that the collimator be connected and extended for localized scanning.

While such a probe may be generally suitable for its intended purposes, its use appears limited, i.e., it cannot provide optimum performance since it does not permit continuous varying of the solid angle of acceptance of the radiation, nor does it provide adequate shielding from the radiation entering from the back of the probe. In this connection it should be appreciated by those skilled in the art that the amount of radioactivity as well as the size and efficiency of the radiation detector within the probe and the solid angle of acceptance established by the probe's collimator determine the count rate. It has been determined that for a probe to be reliable on low count rates the counts in a suspected radioactive location should be at least two times the background level. Thus, in order to achieve optimal tradeoffs between the count rate, sensitivity and directionality, the probe must include some means for continuously varying the solid angle of acceptance of the radiation.

The following U.S. patents relate to collimators and/or apparatus for use with x-ray or other radiation detecting equipment, e.g., x-ray machines, etc: 3,112,402 (Okun et al.), 3,310,675 (Prickett et al.), 3,628,021 (MacDonald), 3,609,370 (Peyser), 3,869,615 (Hoover et al.), 3,919,519 (Stevens), 3,936,646 (Jonker), 4,340,818 (Barnes), 4,419,585 (Strauss et al.), 4,489,426 (Grass), 4,502,147 (Michaels) 4,782,840 (Martin Jr. et al.), and 4,801,803 (Denen et al.).

OBJECTS OF THE INVENTION

It is a general object of this invention to provide a collimating probe and methods of use which overcome the disadvantages of the prior art.

It is a further object of this invention to provide a collimating probe whose solid angle of acceptance can be varied continuously throughout a range defined by maximum and minimum predetermined angles.

It is still a further object of this invention to provide a continuously adjustable collimating probe which is easy to use.

It is yet a further object of this invention to provide a continuously adjustable collimating probe which is simple in construction and which embodies adequate shielding of the detector from the back and sides so that weak signals from a source (e.g., a radioactively tagged tumor) at the orifice of the probe can be reliably detected despite very strong false signals from adjacent structures (e.g., liver, kidney, etc.) very near the sides or back of the probe.

It is yet a further object of this invention to provide methods of use of a continuously adjustable collimating probe for effecting the detection, localization, mapping or imaging of a hidden source of radiation in biological or other applications.

SUMMARY OF THE INVENTION

These and other objects of this invention are achieved by providing a well shielded collimating probe for detecting, localizing, mapping or imaging radiation emanating from a hidden source, e.g., within the body of a living being.

The collimating probe comprises a small probe body formed of a radiation blocking material and arranged to be held adjacent the hidden source, radiation detecting means located within the probe body, aperture means covered by a window means confronting the detecting means through which radiation may pass, and adjustment means for adjusting the solid angle which radiation may pass through the orifice and window means to the detecting means. The solid angle is continuously variable between a predetermined maximum angle and a predetermined minimum angle and vice versa, whereupon the only radiation reaching the detecting means is that which is within the solid angle, despite proximity of strong unscattered signals immediately adjacent to, but outside the solid angle of acceptance.

In accordance with one method the probe is disposed so that the detector means is generally adjacent to the aperture means, adjacent to the hidden source to enable the detection of any radiation within the large solid angle. The probe is moved until the detector detects such radiation. The adjustment means is adjusted to reduce the solid angle and the probe again moved until the detector detects such radiation. That process is repeated until the adjustment means is at or close to the minimum solid angle, whereupon the probe is located confronting the source of radiation, thereby precisely identifying its location. Shielding means prevents false signals from adjacent structures (e.g., liver and kidney), or true signals from other structures (e.g., tumors) from registering on the detector.

DESCRIPTION OF THE DRAWINGS

Other objects and many attendant features of this invention will become readily appreciated as the same becomes better understood by reference to the following detailed description when considered in connection with the accompanying drawings wherein:

FIG. 1 is plan view of one embodiment of a well shielded collimating probe utilizing one type of collimating technique constructed in accordance with this invention;

FIG. 2 is an enlarged sectional view taken along line 2—2 of FIG. 1;

FIG. 3 is a reduced exploded perspective view of the probe shown in FIG. 2;

FIG. 4 is a sectional view taken along line 4—4 of Fig. 2;

FIG. 5 is a sectional view, similar to that of FIG. 2, but showing an alternative embodiment of the collimating probe of FIG. 1;

FIGS. 6A and 6B are sectional views, similar to that of FIG. 2, but showing another alternative embodiment of a collimating probe constructed in accordance with this invention utilizing a second collimating technique and shown in the extended and retracted positions, respectively;

FIG. 7 is a sectional view, similar to that of FIG. 2, but showing yet another alternative embodiment of a collimating probe constructed in accordance with this invention utilizing that second collimating technique;

FIG. 8 is a sectional view of a portion of the embodiment shown in FIG. 7 but at a different collimation setting than that of FIG. 7;

FIG. 9 is a sectional view taken along line 9—9 of Fig. 7;

FIG. 10 is a sectional view, similar to that of FIG. 2, but showing still a further alternative embodiment of a collimating probe constructed in accordance with this invention utilizing the second collimating technique;

FIG. 11 is a sectional view of a portion of the embodiment shown in FIG. 10 but at a different collimation setting than that of FIG. 10;

FIG. 12 is a sectional view, similar to that of FIG. 2, but showing still a further alternative embodiment of a collimating probe constructed in accordance with this invention utilizing a third collimation technique;

FIG. 13 is a sectional view of a portion of the embodiment shown in FIG. 12 but at a different collimation setting than that of FIG. 12;

FIG. 14 is a sectional view taken along line 14—14 of FIG. 12;

FIG. 15 is a sectional view taken along line 15—15 of FIG. 13;

FIG. 16 is an enlarged perspective view of one portion of the probe of FIG. 12 shown in the condition as it is arranged in Fig. 12;

FIG. 17 is an enlarged perspective view of the portion of the probe shown in FIG. 16 but in the condition as it is arranged in FIG. 13;

DETAILED DESCRIPTION OF THE PREFERRED EMBODIMENTS

Figure 21:
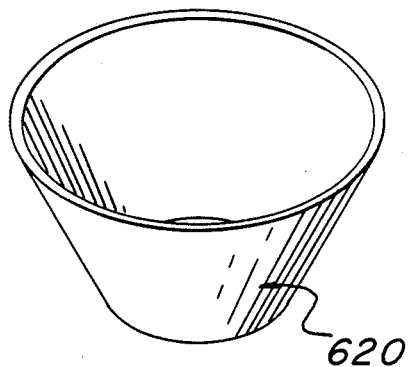
FIG. 21 is a perspective view of a specimen cup insert for use with the accessory shown in FIG. 20.

Referring now to various figures of the drawing where like reference numerals refer to like parts there is shown at 10 in FIG. 1 one embodiment of a collimating probe constructed in accordance with this invention. That probe, like all the other probes to be described herein, is arranged to detect the presence of radiation emanating from a hidden source (not shown), such as tissue tagged with a radioactive isotope, and to provide electrical output signals indicative thereof via a cable or wiring harness 12 to a conventional analyzer 14 or other conventional monitoring or imaging apparatus (not shown). The probe may be used in conjunction with an xy or xy plotter 16 to map the distribution of the radioactivity from the source as a function of the signals provided by the probe. The analyzer preferably includes a conventional RS 232 data port for providing output signals to a printer 18. A computer (not shown) may also be coupled to the probe via a suitable port on the analyzer or on the probe itself. The printer serves as a means to provide a permanent record of tissue assays.

As will be described in considerable detail later the collimating probe 10 includes a radiation detector, of any suitable conventional type, and collimating means to establish the field of view of the probe, i.e., the solid angle of acceptance of the probe's radiation detector. In accordance with the teachings of this invention the collimating means is continuously adjustable to enable the user to readily establish any solid angle of acceptance between a maximum predetermined angle and a minimum predetermined angle that radiation can be accepted by the probe's radiation detector. Adequate shielding in all directions excludes any rays not entering through the collimating means' window.

Moreover, all of the probes of this invention provide significant shielding for radiation from all directions other than that within the solid angle of acceptance by virtue of the materials used and the shape and organization of the probe's components. Thus, the probes of this invention can be used with higher energy radioisotopes, such as Indium 111 and Iodine 131. As will be appreciated by those skilled in the art Indium 111 has approximately ten times the energy of Iodine 125 (e.g., 247 kev versus 25-30 kev). Without good shielding and collimation the use of such high energy materials would be precluded for use in some applications, e.g., detecting tagged cancerous tissue located near the liver, kidneys, or blood vessels, any of which locations would include significant accumulations of the isotope on a non-specific basis. The probes of the subject invention by facilitating precise, continuously variable collimation, enable the localization of a tissue, e.g., a lymph node, containing a very small amount of radiation, e.g., less than a microcurie, lying adjacent to an organ containing several orders of magnitude more radiation, perhaps 2000 microcuries.

The probe 10 shown in FIGS. 1–4 basically comprises a probe body 22 of a generally cylindrical shape and size to be readily held in one's hand. The body 22, as well as other portions of the probe, to be described later, are formed of any suitable radiation blocking material, such as pure tungsten or a tungsten alloy sold under the designation MIL-T-210140D by Teledyne Powder Alloys of Clifton, N.J. 07012.

The probe's body 22 includes a central passageway or internal bore 24 in which a conventional radiation detector 26 is located. The distal or free end of the probe's body 22 which is contiguous with the bore 24 defines a window 28, adjacent the aperture through which radiation is received when the probe is aimed at the suspected source of radiation. In the interests of preventing moisture or debris from gaining ingress into the bore and the detector located therein the window 28 is in the form of a very thin (0.025 mm) sheet of any suitable radiation transmissive material, e.g., beryllium, aluminum, or carbon fiber composite. If desired, however, the window 28 may be open.

Also located within the probe body 22 is an adjustment assembly 30 for extending and retracting the detector/preamplifier assembly 26 within the bore 24 toward and away from the window 28. In the extended position shown by the phantom lines of FIG. 2 the detector/preamplifier assembly is positioned to detect radiation entering the aperture (orifice) covered by window 28 within the maximum solid angle of acceptance shown (by the phantom lines 32). When the detector/preamplifier assembly 26 is retracted from the window to the position shown by the solid lines it can only receive radiation entering the orifice bounded by the window within the minimum solid angle of acceptance (shown by the solid lines designated as 34 in FIG. 2). The movement of the detector/preamplifier assembly 26 within the probe body by the adjustment means 30 is along the central longitudinal axis 36 of the bore and is effected by the rotation of a knob portion of the probe with respect to the probe body 22 about axis 36, as will be described later. Suffice it for now to state that the adjustment means 30 is arranged to move the detector/preamplifier assembly 26 to any longitudinal position along the axis 36 between the fully retracted position and the fully extended position.

In accordance with one, exemplary, preferred embodiment of the invention the ratio of the angle of acceptance between the minimum and maximum is 4 to 1. Accordingly, when the distal or window end of the probe is located approximately 25 mm from a source of radiation and the adjustment means has moved the detector/preamplifier assembly 26 within the internal bore 24 to the extended position, radiation can be received from any source within the circle A (FIG. 1) centered about the axis 36 having an area of approximately 1400 sq. mm. When the adjustment means is adjusted to move the detector/preamplifier assembly the retracted position of the area of the circle B (FIG. 1) from which radiation can be accepted is approximately 350 sq. mm.

It must be pointed out at this juncture that the foregoing angles of acceptance are merely exemplary. This working range of angles of acceptance may be extended to compensate for radioactive decay. A maximum forward detector position at the aperture window for maximum sensitivity may be used when radioactivity is minimal. A maximum retracted detector position may be appropriate with intense radioactive signal. Thus the probe 10, as well as any other probe constructed in accordance with this invention, can be set up to achieve any minimum and maximum solid angle of acceptance at any desired spacing of the probe window from the source of radiation. In clinical use, the working range of angles of acceptance will vary as the radioactivity to be detected varies.

It should be appreciated that when the collimating probe is set for its maximum angle of acceptance, the device is in its maximum sensitivity. Sensitivity decreases as the solid angle of acceptance is reduced. The ability to continuously adjust the solid angle of acceptance by collimation, and hence the sensitivity, enables the probe to be used effectively at any time during a relatively long period of time after the isotope is introduced into the patient.

In typical use of this invention a radioisotope having an energy of in excess of 70 kev is injected into the patient. Within seven days or less the probe can be used to detect, localize and/or map the radiation emanating from that isotope.

The detector/preamplifier assembly 26 can take various forms. One preferred embodiment comprises a radiation detecting crystal 38, such as a cadmium telluride, and an associated solid state preamplifier 40, such as that sold by Amptek Corporation of Bedford, Mass. 01730 under the model designation A-225. Alternatively, as shown in FIG. 5, the detector assembly 26 may comprise a scintillation crystal 42 of any suitable material, e.g., sodium iodide, cesium iodide, bismuth germinate, etc., an associated photomultiplier means such as a silicon photodiode or avalanche photodiode or conventional photomultiplier tube 44, and, when needed, a preamplifier 46. All other details of the probe of FIG. 5 (designated by the reference numeral 20) are the same as that of the probe shown in FIGS. 1-4 and will not be separately described.

The adjustment means 30 for moving the detector assembly 26 of the embodiments of the probe shown in FIGS. 1-5 is best seen in FIGS. 2 and 3 and basically comprises a tracked sleeve 48, a slotted sleeve 50, a follower base 52 and follower pins 54. The tracked sleeve, as can be seen in FIG. 3, is a tubular cylindrical member of thin wall construction. The sleeve 48 is fixedly secured within an annular recess 56 (FIG. 5) in the internal bore 29 of the probe body 22. The sleeve 48 includes a helical recess or track 58 extending about axis 36 in the inner surface or through the full thickness of the sleeve. The slotted sleeve 50 basically comprises a thin walled, cylindrical tubular member whose outside diameter is just slightly less than the inside diameter of the tracked sleeve 48. The slotted sleeve 50 includes a pair of longitudinally extending pin location slots 60 disposed diametrically opposed to each other and parallel to the axis 36. A mounting plate 62 having a central upwardly projecting hub 63 extends into the bottom of the slotted sleeve 50 and is fixedly secured thereto (see FIGS. 2 and 5).

The detector/preamplifier assembly 26 is disposed within the central passageway extending through the slotted sleeve 50 and is supported on the follower base 52. The follower base 52 is a disk-like member which is disposed for longitudinal movement within the slotted sleeve 50. To that end the outer diameter of the follower base is just slightly smaller than the inner diameter of the slotted sleeve 50. The follower base includes a passageway 64 extending diametrically therethrough perpendicular to the axis 36 and in which is located the follower pins 54. A helical biasing spring 66 is disposed within the follower base's passageway between the follower pins 54. This spring biases the follower pins radially outward so that the free end of each pin extends out of the follower base and through an associated slot 60 in the slotted sleeve 50 and into the portion of the helical track 58 contiguous therewith.

As shown clearly in FIGS. 3 and 5 the mounting plate 62 includes an outwardly flanged portion 68 which is disposed within a correspondingly shaped annular recess within the end wall 70 of the probe body 22. An annular recess 72 is also located within the end wall 70 and extending about the annular recess holding flange portion 68. The recess 72 serves to hold an O-ring 74 therein. A base plate 76, in the form of a circular disk, is secured via conventional threaded screws 78 to the end wall 70 of the probe body 22, with the O-ring 72 interposed therebetween. The mounting plate includes a downwardly extending cylindrical hub portion 80 which extends through a central opening 82 in the base plate (see FIG. 4).

With the components secured together as just described, the mounting plate 62 and the slotted sleeve 50 fixedly secured thereto may be rotated about axis 36 with respect to the probe body 22 (and the base plate 76 to which it is fixedly secured). Such rotation moves the detector/preamplifier assembly 26 toward and away from the window 28 (depending upon the direction of rotation) and is effected by the user (e.g., surgeon) rotating an adjustment knob 84 located at the proximal end of the probe. Thus, as can be seen in FIGS. 1-2 and 4-5, the knob is a circular disk-like member which is fixedly secured to the downwardly extending hub portion 80 of the mounting plate. The knob includes a central annular recess 86 in which that hub portion is disposed. The knob 84 is fixedly secured to the mounting plate 62 via plural threaded fasteners (screws) 88. In order to facilitate the grasping (twisting) of the knob with respect to the probe body 22, the outer surface of the knob may be knurled or include flatted portions.

As should be appreciated from the foregoing when the probe body 22 is gripped in the palm of the user and the knob 84 is grasped and rotated (twisted) about axis 36 with respect to the probe body, the tracked sleeve 48 rotates with respect to the slotted sleeve 50. Accordingly, the free end of each of the extending follower pins 54 slides along respective portions of the helical track 58 in the sleeve 48. The longitudinally extending slots 60 in the sleeve 50 prevent the follower base from rotating and hence translate the twisting motion into an up/down motion of the follower base within the sleeve 50, with the direction of such motion depending upon the direction of rotation of the knob 84.

As can be seen in FIG. 2 the mounting plate 62 includes an angled passageway 89 extending therethrough. A similar and coaxial angled passageway 90 extends through the knob 84. The two passageways 89 and 90 are contiguous and form the opening for a cable or wiring harness 12 carrying electrical signals/power between the detector 26 and the analyzer 14. The follower base includes at least one angled hole (not shown) through which the cable 12 from the detector 26 passes. Means, not shown, are provided to seal the passageways 88 and 90 from the ingress of moisture into the interior of the probe. The O-ring 74 also serves to prevent the ingress of moisture into the interior of the probe via the interface between the end wall 70 of the probe body 22 and the contiguous surface of the base plate 76.

In order to ensure that the only radiation received by the detector is that entering through the orifice adjacent window 28, the side wall of the probe body 22 is substantially thick, e.g., 5 to 9 mm of tungsten for shielding Iodine-131 and Indium-111, and 2 to 4 mm tungsten for shielding Technetium 99 m. Moreover, the knob 84 and the base plate are each formed of a radiation blocking material, such as the tungsten alloy making up the probe body 22. The follower base 52 is also formed of tungsten alloy or other radiation shielding material.

It should also be pointed out that the conductors connected between the cadmium telluride crystal and the preamplifier of the embodiment shown in FIGS. 1–4 or between the scintillation crystal, the photomultiplier means and the preamplifier of the embodiment of FIG. 5 are not shown herein in the interest of drawing simplicity.

In order to expedite the aiming of the probe so its distal end (the aperture covered by window 28) can be directed to whatever portion of the body the user wishes to examine, the probe 10 includes a light beam aiming system. That system basically comprises a light source such as an LED 92 (FIG. 3) disposed outside of the probe body 22, and an associated fiber optic or light pipe 94 extending down the length of the body and radially inward into the bore 24 close to the window 28. The free end of the light pipe 96 is disposed on the axis 36 and extends through a central opening in the window 28 on axis 36. The light source is provided via an associated fiberoptic light conductor 98, extending from outside the probe body to minimize electrical current in the probe.

As will thus be appreciated when the probe is positioned adjacent a patient and the light source energized a beam of light will exit from free end 96 of the light pipe coincident with the probe's central axis 36. This beam of light can then be directed at whatever portion of the patient's body is to be centered within the probes' angle of acceptance.

It must be pointed out at this juncture that the light aiming system just described is merely exemplary. Hence, other light generating systems to facilitate aiming of the probe may be incorporated in probe 10 or in any other probe constructed in accordance with this invention.

Operation of the probe 10 is as follows: The probe is adjusted to the maximum solid angle of acceptance and is then brought adjacent the portion of the patient's body to be examined. With the probe at this setting its sensitivity is maximum so that the general location of the emanated radiation can be readily found. The probe's solid angle of acceptance of the probe is the reduced to whichever intermediate setting is desired by the user while monitoring the radiation detected and moving the probe in response to that detected radiation to center the probe over the source. This operation continues until the probe is at its narrowest solid angle of acceptance setting and still receiving radiation. At this point the user can be sure that the source of that radiation is directly opposite the probe's window.

In order to verify that the identified tissue indeed has radioactivity in it, the probes of the subject invention are arranged to be used with an accessory specimen receptacle which is constructed in accordance with another aspect of this invention. Details of that accessory receptacle will be described later. Suffice it for now to state that the receptacle is used as follows: the receptacle is releasably secured to the probe at the probe's window and a small specimen of suspected tissue which the surgeon has removed from the site of the localized radiation is disposed within the receptacle. The probe can then be operated to determine if the specimen does, in fact, contain radioactivity. In accordance with a preferred embodiment of the receptacle it is constructed so that it blocks ambient radiation, i.e., all radiation except for that from the specimen, from passing through the probe's radiation transmissive window for receipt by the detector. The ability of the probe and its accessory receptacle to block stray radiation enables the reliable testing of the specimen for radiation even though the amount of radioactivity in it may be in the microcurie range or less, whereas the probe may be adjacent sources of radiation several orders of magnitude greater.

The embodiments shown in FIGS. 1–5 and described above are merely exemplary of various ways of moving the detector assembly within the probe to continuously adjust the solid angle of acceptance within the scope of this invention. Thus, other mechanisms can be used to achieve that end in accordance with the teachings of this invention.

Figure 6A:
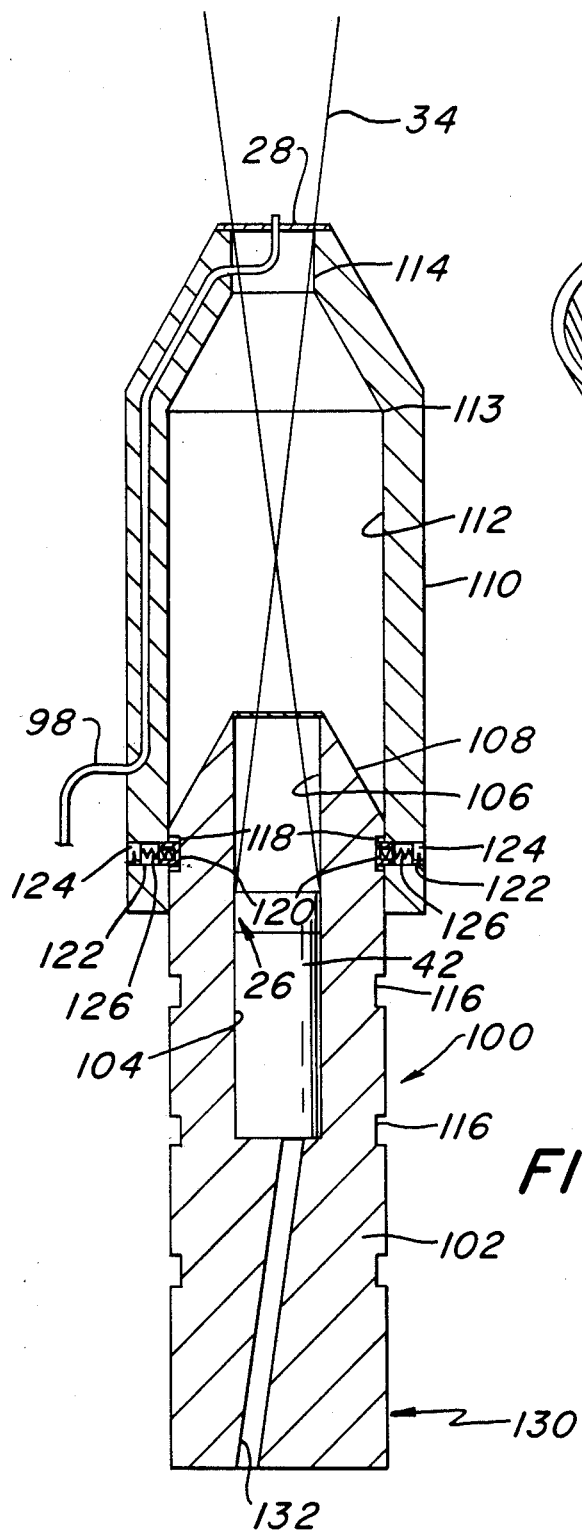

Referring now to FIGS. 6A and 6B, another alternative embodiment of a probe 100 constructed in accordance with this invention is shown. In that embodiment the detector 26 is held stationary and a portion of the probe body having the entrance aperture and window 28, therein is moved with respect to it, to thereby continuously adjust the solid angle of acceptance. Components of probe 100 which are common to the probes described heretofore are given the same reference numbers and their construction, organization and operation will not be repeated. The probe 100 includes a cylindrical tubular probe body 102 formed of a radiation blocking material, such as tungsten alloy, having a central bore 104 in which is fixedly secured the radiation detector 26. In the embodiment shown in FIGS. 6A and 6B the components forming the detector 26 are interconnected together via wires (not shown). The free end of the bore 104, is open at 106. The outer surface of the probe at the free end is tapered at 108.

A movable restrictor sleeve 110 in the form of a tube is disposed about probe body 102. The restrictor sleeve 110 has a central bore 112 whose internal diameter is just slightly larger than the external diameter of the probe body 102. The central bore 112 includes a tapered portion 113 adjacent its free end and which is complementary in shape with the conical surface 108 of the probe body 102. The free end 114 of the central bore 112 is of constant diameter extending about axis 36 to form an outlet or opening over which the window 28 is secured.

Adjustment means 116 are provided for moving the restrictor sleeve 110 and hence the entrance aperture and window 28 toward and away from the detector 26 between the solid line position 32 and the phantom line position 34, and vice versa, as shown in FIGS. 6A and 6B. In particular, the adjustment means 116 basically comprises a helical groove or track 118 extending about the outer periphery of the probe body 102 about axis 36. A pair of follower or guide pins 120 extend into the track 118 from diametrically opposed sides of the probe body 102. The pins 120 are located in respective ones of a pair of diametrically opposed bores 122 extending through the wall of the restrictor sleeve 110. Each follower pin 120 is secured in place within its bore via a respective threaded set screw 124 threadedly engaged at the end of the bore. A helical compression spring 126 is located in each bore between the associated follower pin and set screw to bias the pin radially inward and thus hold the pin's free end within the helical track 118.

The proximal (lower) end of the probe body 102 is in the form of a disk-like adjusting knob 130. The adjusting knob 130 includes an angled central passageway 132 extending therethrough which serves as the means for enabling the wiring harness or cable 12 from the detector assembly 26 to pass out of the probe to the analyzer 14 or to any other suitable means, e.g., computer, plotter, etc. Moisture sealing means (not shown) are provided to prevent the ingress of moisture through the passageway 132.

Operation of probe 100 is as follows: when the probe's sleeve 110 is held in the user's hand and the adjustment knob 130 is rotated or twisted about axis 36, the sleeve and the window 28 mounted thereon will be moved relative to the probe body, i.e., either brought toward or moved away from the detector assembly 26 fixedly secured within the probe body's bore 104, thereby adjusting the solid angle of acceptance of the radiation received through the aperture bounded by window 28 to the detector assembly. Thus, the probe 100 may be used in the same manner as probes 10 and 20 described heretofore.

As will be appreciated by those skilled in the art, when the probe 100 of FIGS. 6A and 6B is disposed so that the restrictor sleeve is at the phantom line position shown in FIG. 6B (the narrowest angle of acceptance position) the detector assembly 26 is susceptible to receive some stray radiation via the side wall of the probe body 102 which is exposed (uncovered) by the extended restrictor sleeve 110, depending upon the thickness of the side wall. Increasing the thickness of the side wall can reduce the magnitude of such stray radiation. However, increasing the thickness of the side wall of the probe body will necessarily increase the outer diameter of the probe 100. Since it is desirable to keep the outer diameter of the probe 110 relatively small so that it can be held comfortably within the user's hand, there are practical limits as to how thick the probe's sidewall can be made. Moreover, increased wall thickness results in a heavier probe, thereby increasing the chance of operator fatigue when the probe is used.

In FIG. 7 there is shown an alternative embodiment of a probe 200 utilizing a movable restrictor to effect the continuous variation of the probe's solid angle of acceptance of radiation. That embodiment makes use of a movable restrictor sleeve of a generally thin walled construction and a probe body of generally thick walled construction. Thus, the combined outer diameter of the probe is still sufficiently small that the probe can be comfortably held in the user's palm. In that embodiment, when the restrictor of the probe is extended for maximum collimation there will be thick side wall portions of the probe's body to block the ingress of radiation therethrough to the detector. However, since the restrictor sleeve is of thin walled construction, additional radiation blocking means are mounted within the probe's restrictor to prevent the ingress of radiation to the detector through the side walls of the restrictor. As with the other embodiments described heretofore, the components which are common to other probe(s) described heretofore are given the same reference numerals.

The body 202 of probe 200 is of a generally cylindrical construction having a central bore 204 therein. The bore extends from the free end 206 of the body 202 to an intermediate location 208. The remainder of the body is solid and forms an adjustment knob 210. The free end portion of the bore is closed off by a radiation transmissive window 212 constructed similarly to window 28 described heretofore. The outer surface 214 of the probe body 202 contiguous with the window 206 is tapered. The detector 26 is fixedly secured at the bottom of the bore 204. A central passageway 216 extends down at an angle to the central axis of the probe and communicates with the outside of the probe. The passageway 216 serves to carry the wiring harness or cable 12 from the detector 26 to the analyzer 14 or any other suitable means, e.g., computer, plotter, etc. Means (not shown) are provided within passageway 216 to serve as a moisture seal to preclude the ingress of moisture into the bore 204.

The restrictor sleeve of the probe 200 is designated by the reference numeral 218 and basically comprises a tubular member of generally thin walled construction and having an internal bore 220 whose inside diameter is just slightly larger than the outside diameter of the probe body 202. The free end of the restrictor sleeve 218 includes a tapered wall portion 222 whose wall thickness is greater than that of the cylindrical portion of the sleeve. A constant diameter central passageway 224 extends through the free end of the restrictor sleeve 218 to form an aperture over which a radiation transmissive window 28 is mounted.

The restrictor sleeve 218 is arranged to be moved toward and away from the detector 26 located within the probe body 202 by an adjustment assembly 226. That adjustment assembly basically comprises a helical track 228 in the periphery of the probe body 202 and extending about axis 36. A pair of follower or guide pins 230 extend through respective diametrically opposed threaded bores 232 in the side wall of restrictor sleeve 218. The pins 230 include external threads thereon to mate with internal threads in the bores 232. Each pin includes a free end which projects inward beyond the inner periphery of the restrictor sleeve 218 and into the helical track 228 portion contiguous therewith.

With knob portion 210 of the probe 200 rotated while its restrictor sleeve 218 is held stationary, depending upon the direction of rotation the sleeve 218 will be either retracted to or extended with respect to the probe body 204, thereby moving the window 28 either toward or away from the detector 26. Thus, when the restrictor sleeve 218 is in the extended position (shown in FIG. 7) the radiation reaching the detector 26 will be located within the minimum solid angle of acceptance shown schematically by the lines denoted by the reference numeral 34. Conversely, when the restrictor sleeve 218 is in the retracted position (shown in FIG. 8) the radiation reaching the detector will be within the maximum solid angle of acceptance shown schematically by the lines denoted by the reference numeral 32.

Inasmuch as the free end portion 214 of the probe body 202 is tapered and the side wall of restrictor sleeve 218 is relatively thin, additional radiation shielding means is provided interposed therebetween to prevent stray radiation from reaching the probe's detector through the tapered side wall of the probe's body. Such means basically comprises a shield in the form of a truncated hollow cone 234 having a relatively thick sidewall formed of a radiation blocking material, e.g., tungsten alloy. The shield 234 includes an open upper end 236 and an open lower end 238. The shield 234 is held at an intermediate position between the tapered free end 214 of the probe body 202 and side wall and free end of the restrictor sleeve 218 via a pair of conical compression springs 240 and 242. Thus, one compression spring 240 is interposed between the inner surface of the shield and the conical outer surface 214 of the probe body 202. The conical spring 242 is interposed between the inner surface of the tapered wall portion 222 of the restrictor sleeve 218 and the outer surface of the shield 234.

As should be appreciated by those skilled in the art the conical shield will always be located approximately midway between the free end of the restrictor sleeve and the free end of the probe body, thereby substantially reducing the magnitude of stray radiation that may reach the detector through the side wall of the restrictor sleeve and the tapered side wall portion of the probe body.

In FIGS. 10 and 11 there is shown yet another alternative embodiment of a probe 300 having a movable restrictor for continuously adjusting the solid angle of acceptance. The probe 300 is similar in construction to probe 200 shown in FIGS. 7-9 except that probe 300 includes a plurality of conical shields instead of a single shield. This embodiment provides even more shielding for stray radiation than the embodiment of FIG. 7.

As before, common components and function of the probes shown in FIGS. 7-9 and FIGS. 10 and 11 are given the same reference numerals herein and their description and operation will not be reiterated. Thus, as can be seen in FIG. 10 the probe 300 includes three conical shields 234 which are mounted within the movable restrictor sleeve 218 between the tapered free end portion 214 of the probe body 202 and the tapered portion 222 of the free end of the sleeve 218. The shields 242 are generally equidistantly spaced, via respective conical springs 302, 304, 306, and 308. In particular, one conical spring 302 is interposed between the conical surface 214 of the probe body 202 and the inner surface of the lowermost of the conical shields 234. The second conical spring 304 is interposed between the outer surface of the lowermost of the shields 234 and the inner surface of the intermediate shield 234. The third conical spring 306 is interposed between the outer surface of the intermediate shield 234 and the inner surface of the uppermost shield 234. Lastly, the fourth conical spring 308 is interposed between the outer surface of the upper shield 234 and the tapered inner conical surface of the free end of the restrictor sleeve 218.

The embodiments shown in FIGS. 6-11 and described above are merely exemplary of various ways of moving the probe's entrance aperture and window with respect to a stationary detector to continuously adjust the solid angle of acceptance within the scope of this invention. Thus, various other mechanisms can be used to achieve that end.

Figure 19:
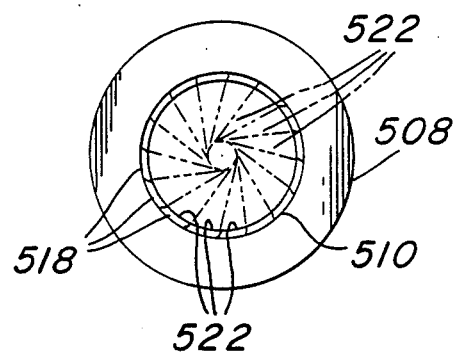
FIG. 19 is a sectional view taken along line 19—19 of FIG. 18.
Figure 18:
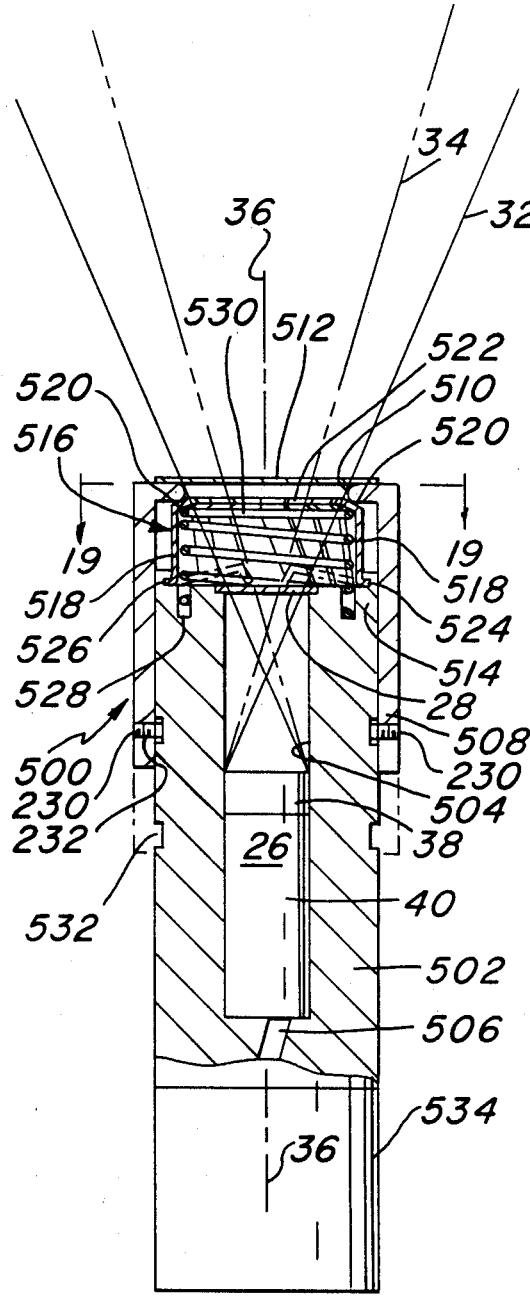
FIG. 18 is a sectional view, similar to that of FIG. 2, but showing still a further alternative embodiment of a collimating probe constructed in accordance with this invention utilizing the third collimation technique.
Figure 20:
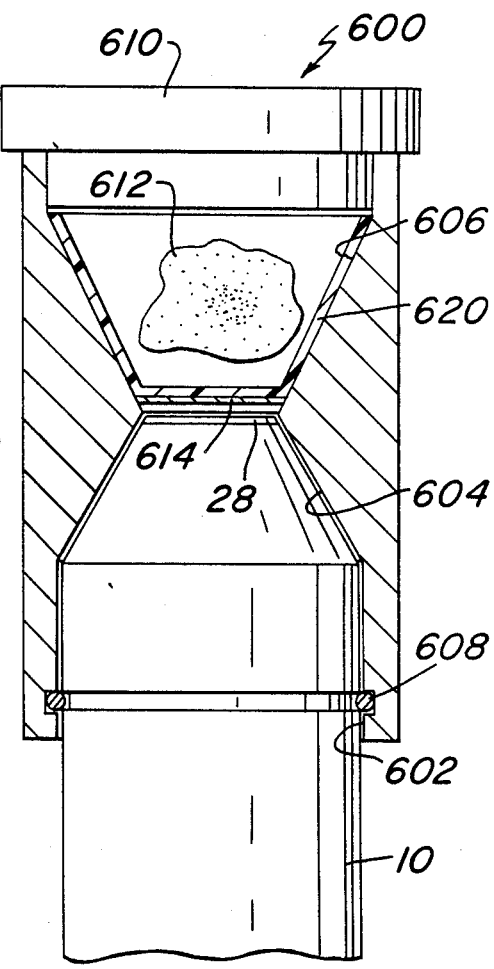
FIG. 20 is an enlarged plan view, partially in section, of an accessory for use with any of the collimating probes of this invention shown releasably secured to one such probe.

In accordance with yet another aspect of this invention the continuous variation of the solid angle of acceptance of the probe's detector can be achieved by the use of an adjustable size entrance aperture. In such an arrangement the entrance aperture through which the radiation will reach the detector is continuously variable in area. One such probe is shown and designated by the reference numeral 400 in FIGS. 12-17. In FIGS. 18-20 there will be shown and described another such embodiment 500. In must be pointed out that those two embodiments are also merely exemplary, and other probes utilizing that concept are also encompassed by this invention.

Like the other probes described heretofore, all common components of the probe 400 and such other probes are given the same reference numerals and their construction and operation will not be reiterated. Thus, as can be seen in FIGS. 12-17 the probe 400 basically comprises a probe body 402 of cylindrical construction and having a central cavity or bore 404 located therein. The detector 26 is located within the bore 404. The free end of the bore 404, also known as the aperture, is closed off by a radiation transmissive window 28, which like that described heretofore serves to prevent the ingress of moisture to the detector while enabling radiation to pass therethrough. The opposite end of the probe body 402 forms a knob 406 which may be knurled at its outer surface or include flattened portions to facilitate the grasping thereof. A central passageway 408 extends through the portion 406 and communicating with the bore 404. The angled passageway 408 serves as the means for carrying the wiring harness or cable 12 between the detector and analyzer or other suitable means, e.g., computer, plotter, etc. Sealing means are provided within that passageway to prevent the ingress of moisture to the interior of the cavity 404.

A tubular sleeve 410 is threadedly mounted on the probe body 402 at the free end thereof. The sleeve 410 includes internal threads 412 mating with external threads 414 on the outer periphery of the tube body 402. The free end of the sleeve 410 includes a conical outer surface 416 and a conical inner surface 418. The opening of the inner conical surface 418 at the free end of the sleeve 410 is closed off by a window 420. The window 420 is formed of a radiation transparent material, such as beryllium, aluminum, carbon or other low atomic number solid material. Interposed between the free end 422 of the probe body 402 and the inner surface 418 of the sleeve 410 is an adjustable diameter collar assembly 424. That assembly basically comprises four collar segments 426 (see FIGS. 16 and 17). Each segment includes a conical outer surface 434 which is arranged to cooperate with the inner conical surface 418 of the sleeve 410 as will be described later. Each collar segment 426-432 comprises a pair of projections 436 (FIG. 16) extending from one side thereof and a pair of correspondingly shaped recesses 438 (FIG. 16) extending into the other side thereof. Thus, the recesses 438 of one segment of the collar are adapted to receive the projections 436 of the immediately adjacent segment. In so doing the collar is arranged to be expanded from the closed position shown in FIGS. 13, 15, and 17 to the open position shown in FIGS. 12, 14, and 16, and vice versa.

The inner surface 440 of each segment is a circular arc of approximately 90°. Accordingly, when the segments are closed so that the collar is in the position shown in FIGS. 13, 15, and 17 a central aperture of a predetermined diameter is formed by the conjoining arc segments 440. This central aperture forms the limiting orifice through which radiation may pass to the detector 26. The segments 426-432 of the collar are each formed of a radiation blocking material, such as tungsten alloy. Accordingly, when the collar 424 is in the closed position its small diameter aperture restricts the radiation which may reach the detector assembly 26, thereby establishing the minimum solid angle of acceptance. This angle is shown schematically by the lines denoted by the reference numeral 34. Conversely when the segments are fully open, that is separated from one another by the maximum distance, their arcuate surfaces 440 define an aperture, which while not completely circular, nevertheless, approximates a circle of enlarged diameter (see FIG. 14). The diameter of the aperture when the collar is in the fully open setting is such that the radiation entering through windows 420 and 28 to the detector are at the maximum solid angle of acceptance and just as if no collar 424 was on the probe.

The means for effecting the continuous adjustment of the collar between the closed and open position and vice versa comprises a compressible circular spring split ring 442 which provides an outward bias force to the segments 426. In particular the ring 442 is disposed within the collar segments 426-432, with the ring engaging the inner cylindrical surface 444 of each such segment. The bias force the ring applies to the segments causes them to move radially outward from axis 36. Thus, the ring tends to move the collar to the open position shown in FIGS. 12, 14 and 16. When the sleeve 410 is rotated about axis 36 in one direction it is retracted with respect to the probe body, thereby causing the sleeve's conical inner surface 418 to engage the conical outer surface 434 of each of the segments 426-432. The continued rotation in that direction applies a radially inward biasing force to the segments against the outward bias force provided by the ring 442, whereupon the segments move closer together. When the sleeve is rotated to the fully retracted position the collar is closed like shown in FIGS. 13, 15 and 17. Conversely, when the sleeve 410 is rotated in the opposite rotational direction to move the sleeve to the fully extended position the collar segments are no longer constrained so that the outward bias force of spring 442 moves the collar segments to the fully opened position shown in FIGS. 12, 14, and 16, whereupon the probe is at the maximum solid angle of acceptance setting.

In FIGS. 18 and 19 there is shown an alternative embodiment of a variable diameter aperture collimating probe. That probe, as mentioned earlier, is designated by the same reference numerals as described heretofore. As can be seen the probe 500 includes a probe body 502 which is a cylindrical member having a central cavity or bore 504. The bore 504 contains the detector 26. The upper or free end of the bore 504 is closed by a radiation transmissive window 28. An angled central passageway 506 extends through the body of the probe 502 into the bore 504 for carrying the wiring harness or cable 12 from the detector to the analyzer 14 or other means, as described heretofore. Sealing means are also located in that opening 506.

A tubular sleeve 508 of thin walled construction and having an internal diameter just slightly greater than the outer diameter of the probe body 502 is mounted on the probe body. The sleeve 508 includes an opening 510 which is of substantially larger diameter than the internal diameter of the cavity 504. The opening 510 is closed by a radiation transparent, moisture impervious window 512 like windows 28 described heretofore. Interposed between the sleeve 508 and the free end 514 of the body portion 502 is adjustment means in the form of an adjustable collar assembly 516.

The collar assembly 516 is arranged to vary the solid angle of acceptance of radiation passing from window 512 to window 28 and to the detector 26 located within the cavity 504. To that end the assembly 516 comprises a plurality of iris like segments 518. The segments conjoin with one another to form a tube-like member. The upper end 520 of each of the segments 518 extends at an angle to the remaining portion of the segment and terminates in an arcuate edge 522. These arcuate edges conjoin with one another to form a circular aperture. The aperture is of variable diameter and forms the adjustable window establishing the solid angle of acceptance of the probe.

To achieve such adjustability the upper end of each of the segments is arranged to be pivoted with respect to its lower end against the bias of a spring (to be described later) from the solid line position shown in FIG. 18 to the phantom line position shown therein. When the segments are in the solid line position shown in FIG. 18 the aperture formed by arcuate edges 522 is at a maximum diameter, thereby establishing the maximum solid angle of acceptance of gamma rays to the probe 500. When the segments 518 are at the inwardly pivoted or phantom line position shown in FIG. 18 the aperture is of considerably reduced diameter as shown schematically by the phantom lines in FIG. 19. Accordingly, when the segments 518 are in the phantom line position shown in FIGS. 18 and 19 the probe is set to establish the minimum solid angle of acceptance (shown schematically by the solid lines 32).

To achieve the pivoting action just described the lower end of each of the segments 518 is flanged and forms a pivot 524 about which the segment may be rotated radially inward or outward. Each segment's pivot 524 is held within an annular recess 526 at the free end 514 of the probe's body portion 502. A second annular recess 528 is located in the free end portion 514 of the probe's body 502. A helical compression spring 530 is interposed between the tapered surface and the top portion of each of the segments 518 and the bottom of the annular recess 528. The pivoting of the segments from the solid line position shown in FIG. 18 to the phantom line position shown therein, and vice versa, is effected by the rotation (twisting) of the sleeve 508 with respect to the body portion 502. To that end the body portion 502 includes a helical track 532 in its outer periphery. A pair of set screw follower pins 230 extend through diametrically opposed threaded bores 232 in the sleeve 508. The free end of each pin is located within the track 232.

The lower portion 534 of the probe's body 502 forms a knob or handle portion which is arranged to be grasped by the user. Thus, its surface may be knurled or include flatted portions to assist the grasping of it. The sleeve 508 may then be rotated with respect to the probe's body 502 to extend or retract the sleeve thereon (depending on the direction of rotation). When the sleeve is rotated to the fully extended position the spring 528 is at its maximum expanded height (shown by the solid lines in FIG. 18). This causes the periphery of the top of the spring to engage the inner surface of the angularly extending portion 520 of each segment 518 to pivot the segments radially outward until the outer surface of the angularly extending portion engages the periphery of the opening 510. In this position the probe is set at the maximum solid angle of acceptance.

Rotation of the sleeve 508 with respect to body portion 502 in the opposite direction retracts the sleeve, whereupon the periphery of the sleeve's opening 510 slides across the tapered outer surface portion 522 of each segment 518. This action causes those segments to pivot about their pivot end 524 in a radially inward direction (towards the central axis 36 of the probe), thereby reducing the diameter of the aperture formed by edges 522. Continued rotation of the sleeve 508 in that direction causes further inward pivoting of each of the segments 518, thereby further reducing the diameter of the aperture until the sleeve is fully retracted, whereupon the diameter of the aperture is at its minimum. In this position the spring is fully compressed.

The embodiments shown in FIGS. 12–19 and described above are merely exemplary of various ways of altering the size of the window with respect to the detector to continuously adjust the solid angle of acceptance. Thus, various other mechanisms can be used to achieve that end in accordance with the teachings of this invention.

In FIG. 20 there is shown the accessory receptacle 600 mentioned heretofore. That receptacle can be shaped to mate for use with any of the probes constructed in accordance with this invention. Moreover, it may be used in conjunction with any radiation detecting probe.

The receptacle 600 basically comprises a tubular member, formed of a radiation blocking material, such as tungsten alloy, and having a central recess 602. The central recess includes a bottom portion designated by the reference numeral 604 and an upper portion designated by the reference numeral 606. The bottom portion 604 of the recess is configured to accept the free (distal) end of any probe constructed in accordance with this invention or otherwise. In the embodiment shown in FIG. 20 the probe is designated by the reference numeral 10. In order to hold the receptacle 600 in place on the probe tip a circular ring-shaped gripping member 608 (e.g., an O-ring or a split ring) is provided and extends into the bore portion 604 to frictionally engage the matching groove in the outer surface of the probe 10. When the receptacle 600 is mounted on the probe 10 as just described the hollow recess portion 606 is located directly over the probe's window 28. The portion 606 serves as a cavity or chamber for holding a specimen 612 to be tested. Disposable accessory specimen cups 620 (FIG. 21) are provided for insertion into chamber 602 to prevent contamination of the chamber's inner surfaces by radioactivity from serial samples of tissue being assayed.

In order to prevent the specimen 612 from falling out and to block any stray radiation from entering the receptacle (and hence gaining ingress to the probe's window) a cap 610, also formed of a radiation blocking material, e.g., tungsten alloy, is provided. The cap may be frictionally fit or threaded so that it does not slip off when it is used. Since the receptacle 600 and its cap are formed of a radiation blocking material stray radiation will be precluded from entering the probe's window. To further that end, the angle of the inner surface of the chamber 608 is approximately that of the probe's maximum solid acceptance (so that the probe is also at its maximum sensitivity). Accordingly, the probe can detect minute amounts of radiation from the specimen notwithstanding the fact that the probe may be located adjacent the source of radiation which is many orders of magnitude greater. The chamber window 614 serves to prevent leakage from the specimen 612 while not obstructing radiation.

If the probe does detect radiation from the specimen the surgeon can feel some degree of assurance that the material which he/she excised is in fact the material which he/she desires to remove. The receptacle 600 can then be removed from the probe and the probe again used to detect if there is any other radiation emanating from the site of the excised tissue or other site(s). Once such other tissue has been located it too can be removed or otherwise treated.

It should be appreciated from the foregoing that the probes of the subject invention offer significant ability to methodically precisely find radioactive tissue within the body of a living being for either a diagnostic or therapeutic, e.g., surgical, purposes. Thus, for example, with the subject collimating probe the surgeon can go from a broad survey setting to a pinpoint (narrowest angle of acceptance) setting, including in the process any intermediate setting, quickly, easily and with a great deal of certainty that the radiation received when the probe is in its pinpoint setting has come from directly in front of the probe and nowhere else, thereby precisely locating the radiation source.

Moreover, it will be appreciated that the probe of the subject invention can be utilized to map or provide imaging of the radiation within the body of the being. Such action can be readily accomplished by using the probe in the survey setting to determine the location of the radioactivity and thereafter adjusting the probe to narrow the angle of acceptance to determine its boundaries. Once this is accomplished the probe may be set to the minimum solid angle of acceptance and the probe moved in a systematic pattern all across the area within the determined boundaries to provide a point by point image of the radiation source or data for mapping the same. In conjunction with the xy or xyz plotter 16, a point-by-point image can be constructed. Thus, for example the three space tracker manufactured by the Polhemus Navigation Sciences Division of McDonnell Douglas Electronics Company of Colchester, Vt. 05446, can be used with these probes to construct 3-dimensional maps of radiation distribution.

It must also be pointed out at this juncture that while the probes of the subject invention have particular utility for medical applications, that is to detect, localize, image and/or map radiation within the body of a living being, e.g., to facilitate cancer surgery, they can also be utilized for nonbiological applications. In fact, the subject probes can be utilized for any application wherein detection, localization, imaging and/or mapping of hidden radiation is desired. Further still the probes of this invention can be constructed to utilize a combination of the various solid angle of acceptance adjustment techniques, e.g., movement of the detector, movement of the aperture, changing the size of the aperture, etc., described heretofore.

Without further elaboration the foregoing will so fully illustrate our invention that others may, by applying current or future knowledge, adopt the same for use under various conditions of service.

What is claimed is:

1. A well shielded collimating probe for detecting radiation emanating from a hidden source, said probe comprising a small probe body formed of a radiation blocking material and arranged to be held adjacent said hidden source, radiation detecting means located within said probe body, window means covering aperture means confronting said detecting means through which radiation may pass, and adjustment means for adjusting the solid angle which radiation may pass through said aperture means to said detecting means, said solid angle being continuously variable between a predetermined maximum angle and a predetermined minimum angle and vice versa, whereupon the only radiation reaching said detecting means is that which is within said solid angle.

2. The collimating probe of claim 1 wherein said aperture means is of a fixed size and wherein the distance between said aperture means and said detecting means within said probe body is adjustable by said adjustment means to establish said solid angle.

3. The collimating probe of claim 2 wherein said adjustment means moves said detecting means within said probe body with respect to said aperture means.

4. The collimating probe of claim 3 wherein said probe body includes a longitudinal axis and wherein said adjustment means is moved with respect to said axis to move said detecting means within said probe body along said axis.

5. The collimating probe of claim 4 wherein said adjustment means comprises a portion of said probe body and coupling means connected to said detecting means, said portion of said probe body and said coupling means cooperating with each other to move said detecting means within said probe body when said probe body portion is moved.

6. The collimating probe of claim 5 wherein said probe body portion is arranged to be rotated about said axis.

7. The collimating probe of claim 6, whereupon the rotation of said probe body portion moves said detecting means either towards said window means or away from said window means, depending upon the direction of rotation of said body portion.

8. The collimating probe of claim 7 wherein said probe body portion and said coupling means include track means, said track means being disposed at a helical angle with respect to said axis, whereupon twisting of said probe body portion about said axis moves said detecting means.

9. The collimating probe of claim 2 wherein said detecting means is fixedly positioned within said probe body and wherein said adjustment means moves said aperture means with respect to said probe body.

10. The collimating probe of claim 9 wherein said probe body includes a longitudinal axis and wherein said adjustment means comprises sleeve means having a free end at which said aperture means is located and which is moved with respect to said axis to move said window means with respect to said probe body along said axis.

11. The collimating probe of claim 10 wherein said probe body is an elongated tubular member having a radiation receiving aperture located at one end thereof and through which said axis passes, said detecting means being located within said tubular portion and confronting said inlet, said sleeve means comprising a tubular body formed of a radiation blocking material and having a free end at which said window means is located.

12. The collimating probe of claim 11 wherein said sleeve means comprises a thin walled portion extending about said probe body portion, said probe body portion being thicker walled than said sleeve means.

13. The collimating probe of claim 12 wherein said free end of said sleeve means is in the form of an inwardly directed annular flange, with said aperture means being located within the interior of said flange, said sleeve means additionally comprises radiation blocking means located therein and interposed between said inlet of said probe body and said annular flange of said sleeve means.

14. The collimating probe of claim 13 wherein said radiation blocking means comprises at least one conical member.

15. The collimating probe of claim 14 wherein said conical member is mounted by positioning means substantially centered between said flange of said sleeve means and said inlet of said probe body.

16. The collimating probe of claim 15 wherein said positioning means comprises spring means.

17. The collimating probe of claim 16 wherein said radiation blocking means comprises a plurality of conical members, said spring means supporting said members at generally equidistantly spaced locations between said flange of said sleeve means and said inlet of said probe body.

18. The collimating probe of claim 9 wherein said probe body includes a longitudinal axis and wherein said adjustment means comprises collar means having a radiation transmissive passageway extending therethrough forming said window means, said collar means being located within said probe body and moveable with respect to said axis.

19. The collimating probe of claim 2 wherein said detecting means is fixedly positioned within said probe body and wherein window means comprises a first portion formed of a material which blocks said radiation and a second portion including a radiation transmissive aperture which is adjustable in size covered by a window through which said radiation may pass unblocked, said adjustment means serving to change the size of said aperture.

20. The collimating probe of claim 19 wherein said first portion of said aperture means comprises a plurality of arcuate members coupled to one another and forming an opening of adjustable internal diameter, said opening defining said window.

21. The collimating probe of claim 1 additionally comprising light source means for directing a beam of light out of said probe adjacent said window means to facilitate the location of said probe adjacent said source of radiation.

22. The collimating probe of claim 21 wherein said light source comprise a fiber optic light transmissive member having a free end disposed centered within said window means.

23. The collimating probe of claim 1 additionally comprising receptacle means arranged for releasable securement to said probe body at said window means.

24. The collimating probe of claim 23 wherein said receptacle means comprises a cavity therein for receipt of a specimen of material to detect the presence of radiation emanating therefrom.

25. The collimating probe of claim 24 additionally comprising at least one disposable liner for said cavity.

26. The collimating probe of claim 24 wherein said receptacle means is formed of a radiation blocking material, and includes wall means disposed at the bottom of said cavity means through which radiation may pass unblocked, said wall means being located confronting said window means when said receptacle means is secured to said probe.

27. A method of detecting and localizing radiation emanating from a hidden source utilizing a collimating probe, said probe comprising a small probe body formed of a radiation blocking material, radiation detecting means located within said probe body, window means confronting said detecting means through which radiation may pass, and adjustment means for adjusting the solid angle which radiation may pass through said window means to said detecting means, said solid angle being continuously variable between a predetermined maximum angle and a predetermined minimum angle and vice versa, whereupon the only radiation reaching said detecting means is that which is within said solid angle, said method comprising the steps of adjusting said adjustment means so that said solid angle is at or close to said maximum solid angle, disposing said probe so that said window means is generally adjacent said hidden source to enable said detector to detect any radiation within said solid angle, moving said probe until said detector detects such radiation, adjusting said adjustment means to reduce said solid angle and moving said probe with respect to said source of radiation until said detector detects such radiation, continuing said process until said adjustment means is at or close to said minimum solid angle, whereupon said probe is located confronting said source of radiation to precisely identify its location.

28. The method of claim 27 wherein said radiation source is located within the body of a living being.

29. The method of claim 28 wherein said radiation source is introduced into said body for a diagnostic purpose.

30. The method of claim 29 wherein said detected radiation is used to provide a map or image of said radiation source within said body.

31. The method of claim 30 additionally comprising utilizing a plotter capable of plotting in at least an x and y direction in conjunction with said probe to provide a map of the distribution of radioactivity emanated by said source of radiation.

32. The method of claim 29 additionally utilizing light means associated with said probe, said light means providing a beam of light from said window means to facilitate the aiming of said window means at said source of radiation.

33. The method of claim 29 wherein said detection and localization of the radiation is used for guiding a percutaneous biopsy.

34. The method of claim 29 wherein said detection and localization of the radiation is used for guiding radiation therapy.

35. The method of claim 29 wherein said diagnostic purpose includes nuclear medicine imaging of a conventional and/or tomographic type.

36. The method of claim 28 wherein said radiation source is introduced into said body for a therapeutic purpose.

37. The method of claim 36 wherein tissue of said being contiguous with or bearing said radiation source is removed from the body of said being after said source has been localized.

38. The method of claim 37 additionally comprising the steps of utilizing receptacle means with said probe after at least a portion of said tissue has been removed from said being, said receptacle means being releasably secured to said probe at said window means and comprising a cavity therein, disposing said portion of tissue within said cavity and operating said probe to detect the presence of radiation emanating from said portion of tissue.

39. The method of claim 36 additionally utilizing light means associated with said probe, said light means providing a beam of light from said window means to facilitate the aiming of said window means at said source of radiation.

40. The method of claim 28 wherein said radiation source is located within tissue of a living being to provide an assay thereof.

41. The method of claim 40 additionally comprising providing a permanent record of said tissue assay.

42. The method of claim 41 wherein said tissue is removed from said body for said assay.

43. The method of claim 28 wherein said radiation source is introduced into the body of a living being at a predetermined time and wherein said detection and localization of said radiation from said body is accomplished within less than seven days from said predetermined time.

44. The method of claim 28 wherein said radiation source is introduced into the body of a living being and has an energy in excess of approximately 70 kev.

45. The method of claim 27 additionally utilizing light means associated with said probe, said light means providing a beam of light from said window means to facilitate the aiming of said window means at said source of radiation.

* * * * *